United States Patent [19]

Browner et al.

[11] Patent Number: 5,300,071

[45] Date of Patent: Apr. 5, 1994

[54] PELVIC STABILIZER

[75] Inventors: Bruce D. Browner, West Hartford, Conn.; Richard H. Clewett, Los Angeles, Calif.

[73] Assignee: Ace Medical Company, Los Angeles, Calif.

[21] Appl. No.: 977,490

[22] Filed: Nov. 17, 1992

[51] Int. Cl.$^5$ .............................................. A61F 5/04
[52] U.S. Cl. ........................................ 606/57; 606/54; 606/59
[58] Field of Search .................. 606/57, 58, 59, 54, 606/55, 76, 96, 97, 98, 104, 105, 130, 60; 602/32, 36, 37, 12, 16

[56] References Cited

U.S. PATENT DOCUMENTS

| | | | |
|---|---|---|---|
| 1,967,471 | 7/1934 | Ettinger | 602/37 |
| 2,002,021 | 5/1935 | Rouse | 606/105 |
| 2,200,407 | 5/1940 | Anderson | 602/38 |
| 2,706,475 | 4/1955 | Reynolds, Jr. | 602/37 |
| 3,809,074 | 5/1974 | De Moude | 602/37 |
| 3,865,105 | 1/1975 | Lode | 606/61 |
| 4,024,860 | 5/1977 | Chelnokov et al. | 602/32 |
| 4,361,144 | 11/1982 | Slätis et al. | 606/57 |
| 4,444,179 | 4/1984 | Trippi | 602/37 |
| 4,548,199 | 10/1985 | Agee | 606/57 |
| 4,615,338 | 10/1986 | Ilizarov et al. | 606/59 |
| 4,662,365 | 5/1987 | Gotzen et al. | 606/54 |
| 4,667,660 | 5/1987 | Eingorn | 602/37 |
| 4,895,141 | 1/1990 | Koeneman et al. | 606/54 |
| 5,042,462 | 8/1991 | Bremer | 128/75 |
| 5,141,512 | 8/1992 | Farmer et al. | 606/87 |
| 5,176,679 | 1/1993 | Lin | 606/61 |
| 5,196,012 | 3/1993 | Malka | 606/54 |

FOREIGN PATENT DOCUMENTS 1149960  4/1985  U.S.S.R. ...................... 606/54

OTHER PUBLICATIONS

Reinhold Ganz, M. D., Robert J. Krushell, M. D., Roland P. Jakob, M. D., Jürg Küffer, "The Antishcok Pelvic Clamp", *Clinical Orthopaedics and Related Research*, Jun. 1991 pp. 71-78.

*Primary Examiner*—Stephen C. Pellegrino
*Assistant Examiner*—Guy V. Tucker
*Attorney, Agent, or Firm*—Kinney & Lange

[57] ABSTRACT

A pelvic stabilizer for quickly stabilizing fractures of the human pelvis and preventing excessive blood loss. The pelvic stabilizer comprises first and second curved arms which are rotatably attached to each other at first ends by an adjustable locking mechanism. The locking mechanism permits free second ends of the first and second curved arms to be adjustably spaced from each other. A first mounting pin and a second mounting pin are adjustably attached at the second ends of the first and second curved arms respectively.

10 Claims, 2 Drawing Sheets

PELVIC STABILIZER

BACKGROUND OF THE INVENTION

The following invention relates to the mechanical compression and stabilization of pelvic fractures and, in particular, to an apparatus for rapidly stabilizing fractures of the pelvis to help reduce blood loss.

The human pelvis can be fractured from severe impacts such as those that occur in traffic accidents, falls and industrial accidents. When such a fracture occurs, it is usually accompanied by severe pain and a great deal of blood loss. In many cases, prompt action to stabilize the fracture must be taken in order to prevent the loss of life.

Among the ways in which such fractures are treated is through the use of an external fixator which is applied over the pelvis. The external fixator compresses the pelvis to close the fracture and firmly hold the pelvis in place until it has healed. Previous external fixators have employed a variety of designs, many of which comprise a plurality of interconnected bars. One such design, shown in the Slätis et al. U.S. Pat. No. 4,361,144, utilizes a trapezoidal frame having two protrusions which can be applied over the pelvis and a threaded adjustment mechanism which is used to compress the pelvis.

A problem with most such external fixators is that they take a great deal of time to properly adjust and apply over the pelvis, resulting in excessive blood loss. In addition, many such devices require more than one person and a considerable amount of dexterity to operate. Further, many have a tightening mechanism which cannot be quickly operated to hold the pelvis in place. While such devices may be suitable for long-term stability during healing, they are not well suited for emergency and short-term applications where speed in stabilization is important.

SUMMARY OF THE INVENTION

The present invention provides an apparatus that is capable of quickly stabilizing fractures of the human pelvis. The apparatus comprises first and second curved arms, attached to each other at a first end by an adjustable locking mechanism. Mounting pins are adjustably attached to a second end of each of the first and second curved arms.

Preferably, the locking mechanism permits the second ends of the curved arms to be adjustably spaced from each other and the pelvic stabilizer to be opened and closed. The locking mechanism can be tightened by a tightening knob to hold the first and second curved arms in a fixed, desired position. When tightened, the locking mechanism allows the second ends of the curved arms to move toward each other, but prevents them from moving apart. This ratchet-like feature permits the apparatus to be quickly and easily placed into position about the pelvis.

Preferably, the mounting pins are attached at the second end of each curved arm in a manner permitting them to be angularly adjusted in the plane of the curved arm to which they are attached. In addition, each mounting pin is threaded so that it may be adjusted longitudinally in the plane of the curved arm to which it is attached. Thus, the mounting pins can be easily and quickly adjusted for application over the pelvis and the pelvic stabilizer can be closed to compress and stabilize fractures of the pelvis in a minimal amount of time.

DETAILED DESCRIPTION OF THE PREFERRED EMBODIMENTS

Figure 1:
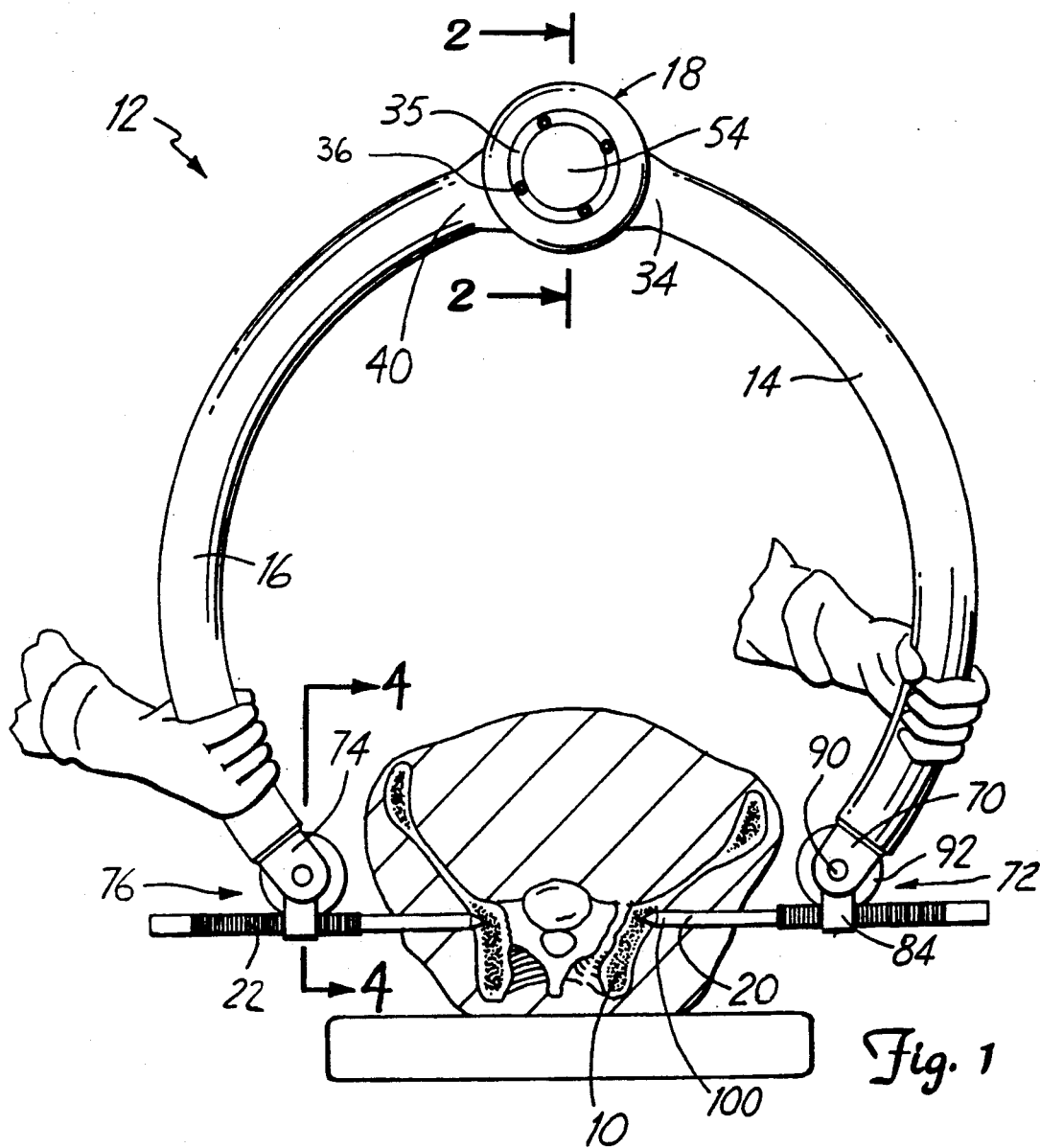
FIG. 1 is a front plan view of the pelvic stabilizer of the present invention applied over a human pelvis.

A human pelvis 10 having a pelvic stabilizer 12 of the present invention applied thereto is shown in FIG. 1. The pelvic stabilizer 12 comprises a first curved arm 14 and a second curved arm 16, which are preferably fabricated from a lightweight metal such as aluminum, joined by an adjustable locking mechanism 18. A first mounting pin 20 and a second mounting pin 22, which are preferably constructed of titanium, are attached to the first curved arm 14 and the second curved arm 16 respectively.

Figure 2:
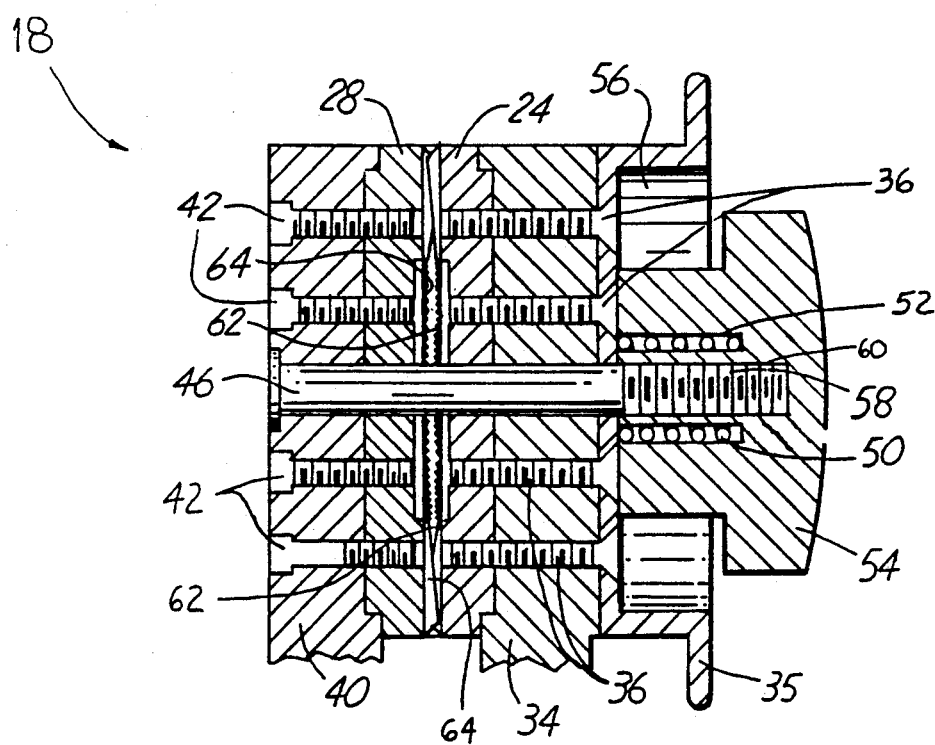
FIG. 2 is a sectional view of a portion of the pelvic stabilizer taken along the line 2—2 of FIG. 1.

The adjustable locking mechanism 18, shown in FIG. 2, comprises a generally circular first ratchet plate 24 and a generally circular second ratchet plate 28. The first ratchet plate 24 is rigidly attached to a first end 34 of the first curved arm 14 and to a hollow cylinder 35 by a plurality of bolts 36 which are equally spaced around the first ratchet plate 24. Each bolt 36 extends through an aperture in the hollow cylinder 35, a hole in the first end 34 of the first curved arm 14 and into the first ratchet plate 24 to assemble the cylinder 35 and the first ratchet plate 24 to the first end 34. The second ratchet plate 28 is rigidly attached to a first end 40 of the second curved arm 16 by a plurality of bolts 42 which are equally spaced around the second ratchet plate 28. Each bolt 42 extends through a hole in the first end 40 of the second arm 16 and into the second ratchet plate 28.

Figure 3:
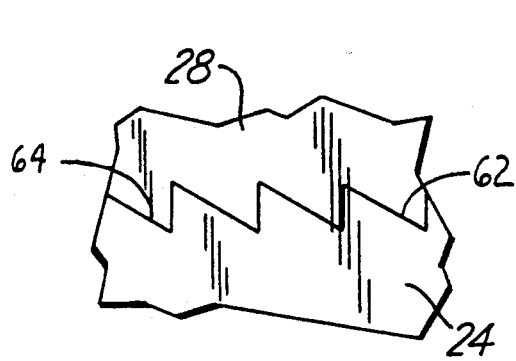
FIG. 3 is an enlarged view of a portion of a ratchet plate of the present invention.

A bolt 46 extends through central holes in the second arm 16, the second ratchet plate 28, the first ratchet plate 24, the first arm 14 and the hollow cylinder 35. A spring 50, through which the bolt 46 also extends, rests in both a recess 52 in a tightening knob 54 and a corresponding recess 56 in the hollow cylinder 35. A threaded first end 58 of the bolt 46 is fastened to a threaded bore 60 in the knob 54 and the knob 54 is tightened until a first surface 62 of the first ratchet plate 24 contacts a first surface 64 of the second ratchet plate 28. The first surfaces 62, 64 of the first and second ratchet plates 24, 28 respectively are serrated, as shown in FIG. 3, such that the first ratchet plate 24 can be rotated in only one direction with respect to the second ratchet plate 28 when the ratchet plates 24, 28 are in close contact.

The first mounting pin 20 is attached to a second end 70 of the first curved arm 14 by a first pin holder 72 and the second mounting pin 22 is attached to a second end 74 of the second curved arm 16 by a second pin holder 76. The first pin holder 72, shown in FIG. 4, and the second pin holder 76 have substantially the same construction and each comprises a generally circular first plate 80, a generally circular second plate 82 and a holding block 84 having a threaded bore 85 therethrough. The first and second mounting pins 20, 22 are threadably fastened to the bores 85 of the first and second pin holders 72, 76 respectively so that rotational movement of a pin causes axial movement thereof.

Figure 4:
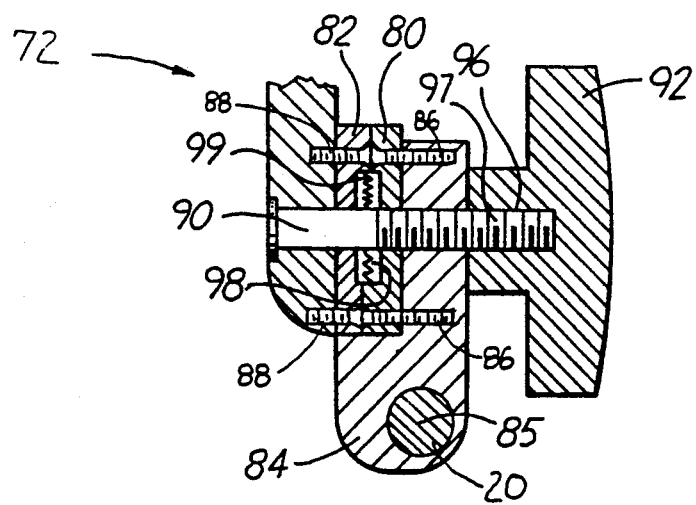
FIG. 4 is a sectional view of a portion of the pelvic stabilizer taken along the line 4—4 of FIG. 1.

Referring to FIG. 4, the first plate 80 is rigidly attached to the holding block 84 by a pair of screws 86 and the second plate 82 is rigidly attached to the first arm 14 near its second end 70 by a second pair of screws 88. A bolt 90 extends through central apertures in the first arm 14, the second plate 82, the first plate 80 and the holding block 84. A tightening knob 92 having a threaded bore 96 therein is threaded onto a threaded first end 97 of the bolt 90. The knob 92 can be tightened so that the first plate 80 and the second plate 82 are brought into tight contact with each other.

Figure 5:
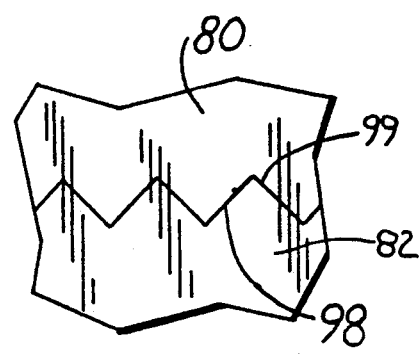
FIG. 5 is an enlarged view of a portion of a pin holder plate of the present invention.

Both a first side 98 of the first plate 80 and a facing first side 99 of the second plate 82 are serrated, as shown in FIG. 5, such that the first and second plates 80, 82 are prevented from rotating with respect to each other when the tightening knob 92 is tightened. When the tightening knob 92 is loosened, the first plate 80 can be rotated in either direction with respect to the second plate 82, permitting the rotation of the holding block 84 and the first mounting pin 20 in the plane of the first curved arm 14. The first mounting pin 20 is threaded along a substantial portion of its length and is threaded into the bore 85 in the holding block 84 so that a pointed first end 100 extends through the holding block 84 a desired distance. Thus, the first pin holder 72 and the second pin holder 76 permit the first and second mounting pins 20, 22 to be both angularly adjusted in the plane of the first and second curved arms 14, 16 and longitudinally adjusted with respect to the first and second pin holders 72, 76 respectively.

In use, the second ends 70, 74 of the first and second curved arms 14, 16 are spaced from each other so that the pelvis 10 can fit therebetween. The tightening knob 54 is tightened against the hollow cylinder 35 and the pelvic stabilizer 12 is placed in a position about the pelvis 10 similar to that shown in FIG. 1. The first and second pin holders 72, 76 are adjusted so that the first mounting pin 20 and the second mounting pin 22 are placed in a desired position relative to the pelvis 10. The tightening knobs 92 on both the first pin holder 72 and the second pin holder 76 are then tightened to hold the mounting pins 20, 22 in place. The second end 70 of the first curved arm 14 and the second end 74 of the second curved arm 16 are then moved toward each other.

The serrations on the first ratchet plate 24 and the second ratchet plate 28 are shaped such that when the knob 54 is tightened, the first ratchet plate 24 can be rotated with respect to the second ratchet plate 28 only in a direction permitting the second ends 70, 74 of the first and second curved arms 14, 16 to move toward each other. As the ratchet plates 24, 28 rotate with respect to each other, the first sides 62, 64 of the plates cam against each other against the bias of the spring 50 until the apex of each serration on the first surface 62 passes the apex of the corresponding serration of the first surface 64 and the spring 56 pushes the plates 24, 28 together. This continues until the second ends 70, 74 of the curved arms 14, 16 are in the desired position with respect to the pelvis 10. The first and second ratchet plates 24, 28 cannot rotate with respect to each other in the opposite direction that allows the second ends 70, 74 of the arms 14, 16 to move away from each other unless the knob 54 is loosened, permitting the plates 24, 28 to be manually moved away from each other.

The first ends 100 of the first and second mounting pins 20, 22 are sharp so that they are able to penetrate the skin and grip the pelvis 10. The second ends 70, 74 of the curved arms 14, 16 are moved toward each other to compress and coarsely stabilize the pelvis 10. The first and second mounting pins 20, 22 may be axially adjusted to provide fine adjustment of the pelvis 10, thereby completing the stabilization.

The pin holders 72, 76 of the present invention are described as permitting angular movement of the mounting pins 20, 22 in the plane of the first and second curved arms 14, 16 only. However, mounting pin holders can be used that permit movement in other directions as well. In addition, the second ends 70, 74 of the first and second curved members 14, 16 can be moved relative to each other through the use of other mechanisms such as a ratchet comprising a wheel and pawl, instead of the first and second ratchet plates 24, 28.

Although the present invention has been described with reference to preferred embodiments, workers skilled in the art will recognize that changes may be made in form and detail without departing from the spirit and scope of the invention.

What is claimed is:

1. A pelvic stabilizer for compressing and stabilizing fractures of a human pelvic bone, the stabilizer comprising:

a first arm having a first end and a second end;
a second arm having a first end and a second end;
adjustable locking means attaching the first end of the first arm to the first end of the second arm and permitting relative rotational movement of the first and second arms, the adjustable locking means including a first ratchet face supported at the first end of the first arm, a second ratchet face supported at the first end of the second arm and bias means for biasing the first and second ratchet faces together when in a first position and allowing the first and second ratchet faces to be spaced from each other when in a second position, the first and second ratchet faces being so disposed and arranged to each other to permit relative rotational movement of the first and second arms in a first direction while substantially preventing relative rotational movement of the first and second arms in an opposite direction when the bias means is in the first position; and
a first adjustable pin assembly mounted on the second end of the first arm and a second adjustable pin assembly mounted on the second end of the second arm, the first and second adjustable pin assemblies being operable to engage the pelvic bone so that relative rotational movement of the first and second arms permits compression of the pelvic bone fracture.

2. The apparatus of claim 1 wherein the first and second ratchet faces have first surfaces engagable to cam against each other to permit rotation in the first direction and second surfaces engagable to lock against each other to substantially prevent rotation in the opposite direction.

3. The apparatus of claim 1 wherein the first and second adjustable pin assemblies each comprises a mounting pin and a mounting pin holder.

4. The apparatus of claim 3 wherein each mounting pin holder includes a first serrated face supported by a respective arm, a second serrated face, a holding block and tightening means for pressing together the first and second serrated faces when in a first position to prevent relative rotational movement between the respective arm and the holding block and allowing the first and second serrated faces to be spaced from each other when in a second position to permit relative rotational movement between the respective arm and the holding block, each respective mounting pin being mounted to a respective holding block.

5. The apparatus of claim 4 wherein each mounting block has a threaded bore therein into which the respective mounting pin can be threadably mounted.

6. The apparatus of claim 4 wherein each tightening means comprises a threaded bolt and a knob having a threaded bore therein.

7. The apparatus of claim 3 wherein the mounting pins are fabricated from titanium.

8. The apparatus of claim 1 wherein the first and second arms are curved so that the respective second ends partially face each other.

9. The apparatus of claim 1 wherein the first arm and the second arm are fabricated from aluminum.

10. The apparatus of claim 1 wherein the bias means comprises a spring, a threaded bolt and a knob having a threaded bore therein.

* * * * *